(12) United States Patent  (10) Patent No.: US 7,686,832 B2
Jackson  (45) Date of Patent: Mar. 30, 2010

(54) IMPLANT FOR SPINAL STABILIZATION AND ITS METHOD OF USE

(75) Inventor: Benjamin L. Jackson, Chadds Ford, PA (US)

(73) Assignee: Synthes USA, LLC, West Chester, PA (US)

( * ) Notice: Subject to any disclaimer, the term of this patent is extended or adjusted under 35 U.S.C. 154(b) by 337 days.

(21) Appl. No.: 11/448,308

(22) Filed: Jun. 6, 2006

(65) Prior Publication Data

US 2007/0016303 A1 Jan. 18, 2007

Related U.S. Application Data

(60) Provisional application No. 60/688,359, filed on Jun. 6, 2005.

(51) Int. Cl.
*A61B 17/88* (2006.01)
(52) U.S. Cl. .............. 606/249; 623/17.11; 411/250; 411/352; 411/356; 411/362; 411/363; 411/364; 411/508
(58) Field of Classification Search .......... 606/279, 606/74, 304, 310; 623/17.11; 411/250, 352, 411/356, 360, 362, 363, 364, 508
See application file for complete search history.

(56) References Cited

U.S. PATENT DOCUMENTS

| | | | | |
|---|---|---|---|---|
| 2,088,637 | A * | 8/1937 | Cooke | 411/360 |
| 5,496,318 | A * | 3/1996 | Howland et al. | 606/249 |
| 5,534,030 | A | 7/1996 | Navarro et al. | |
| 6,025,538 | A * | 2/2000 | Yaccarino, III | 128/898 |
| 6,375,682 | B1 | 4/2002 | Fleischmann et al. | |
| 6,419,704 | B1 | 7/2002 | Ferree | |
| 6,626,944 | B1 * | 9/2003 | Taylor | 623/17.16 |
| 6,666,889 | B1 * | 12/2003 | Commarmond | 623/17.11 |
| 6,796,983 | B1 | 9/2004 | Zucherman et al. | |
| 6,824,565 | B2 | 11/2004 | Muhanna et al. | |
| 6,843,804 | B2 * | 1/2005 | Bryan | 623/17.11 |
| 7,125,425 | B2 * | 10/2006 | Foley et al. | 623/17.16 |
| 2002/0099443 | A1 | 7/2002 | Messerli et al. | |
| 2002/0120335 | A1 | 8/2002 | Angelucci et al. | |
| 2004/0162616 | A1 * | 8/2004 | Simonton et al. | 623/17.11 |
| 2005/0055031 | A1 | 3/2005 | Lim | |
| 2008/0140126 | A1 * | 6/2008 | Ferree | 606/279 |
| 2008/0177306 | A1 * | 7/2008 | Lamborne et al. | 606/246 |

FOREIGN PATENT DOCUMENTS

| | | |
|---|---|---|
| EP | 0 322 334 | 6/1989 |
| FR | 2 730 156 | 8/1996 |
| JP | 09075381 | 3/1997 |
| WO | WO 2004/016205 | 2/2004 |
| WO | WO 2004/073532 | 9/2004 |

* cited by examiner

*Primary Examiner*—Thomas C Barrett
*Assistant Examiner*—David W Bates
(74) *Attorney, Agent, or Firm*—Stroock & Stroock & Lavan LLP

(57) ABSTRACT

A generally rectangular intra-spinous spacer preferably made of bone material advantageously has a low potential for bone fusion. The spacer has depressions sized and positioned on opposite sides to receive spinal processes. The depressions reduce the amount of bone-to-spinal process contact. A fixation strap of the spacer secured either to both the superior and inferior spinous processes or to only one of the superior or inferior processes laterally maintains the implanted position of the spacer and limits either flexion and extension, just flexion, or just extension.

15 Claims, 8 Drawing Sheets

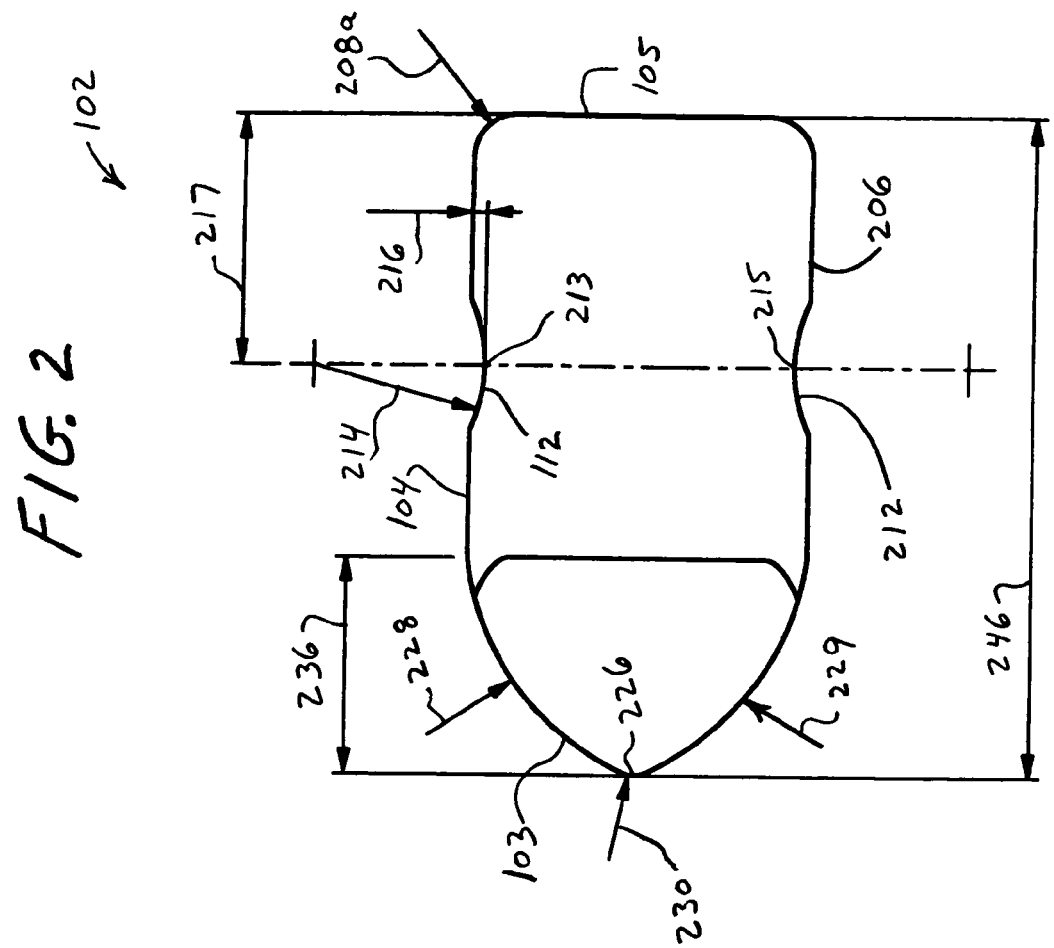
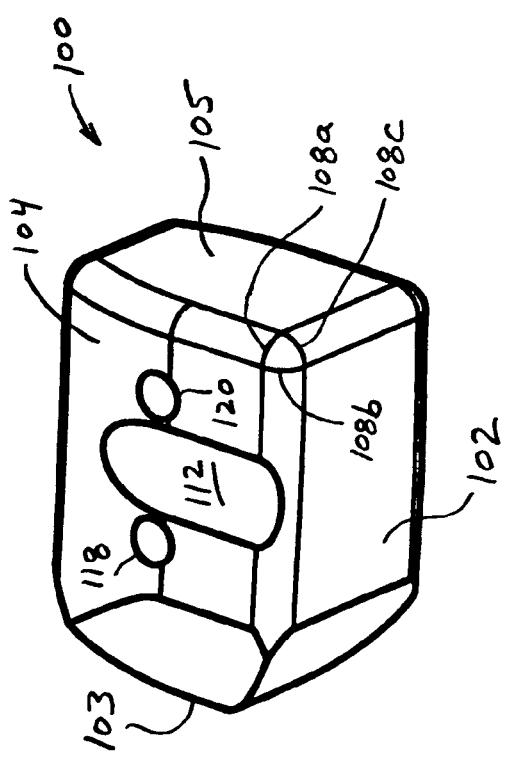

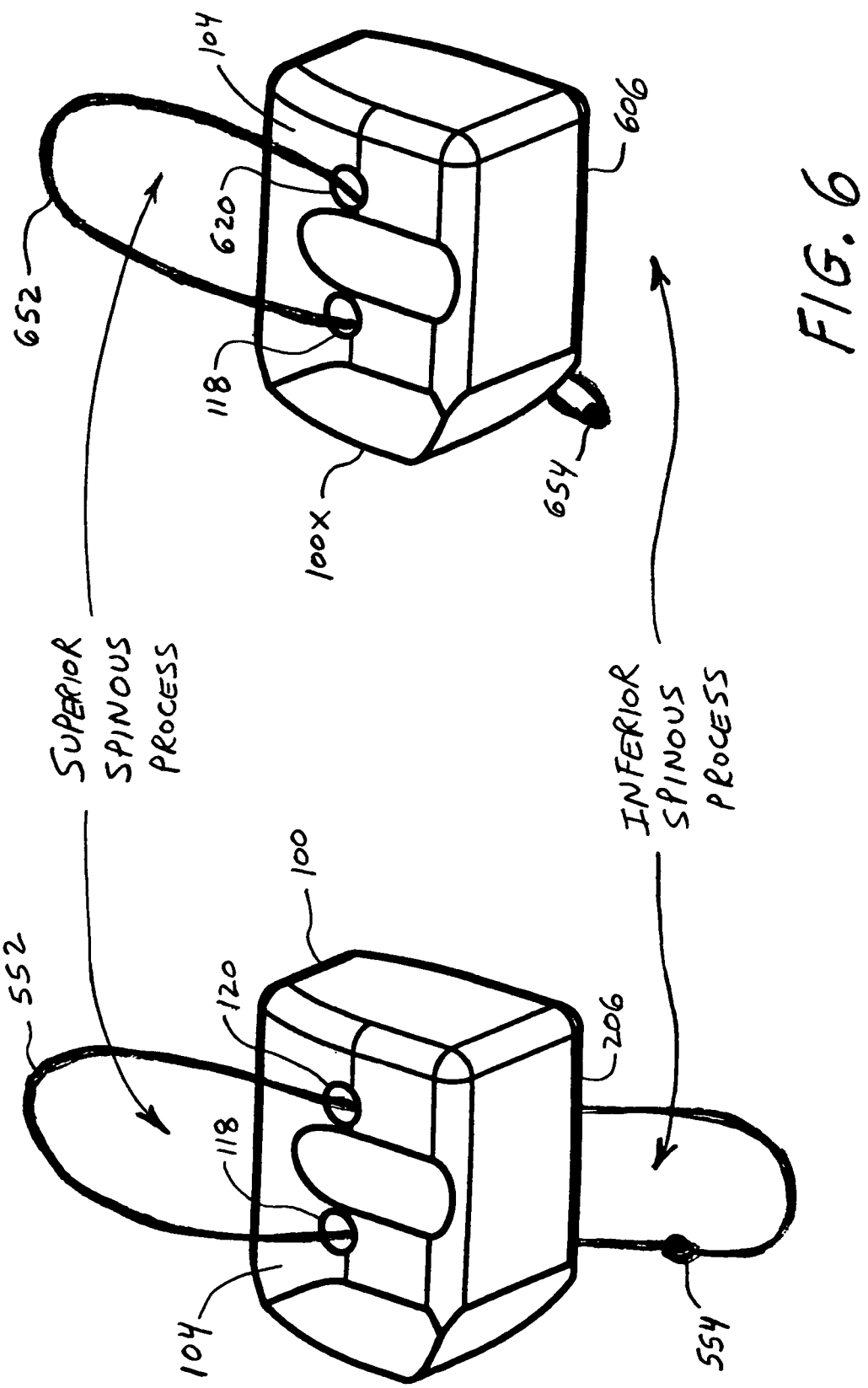

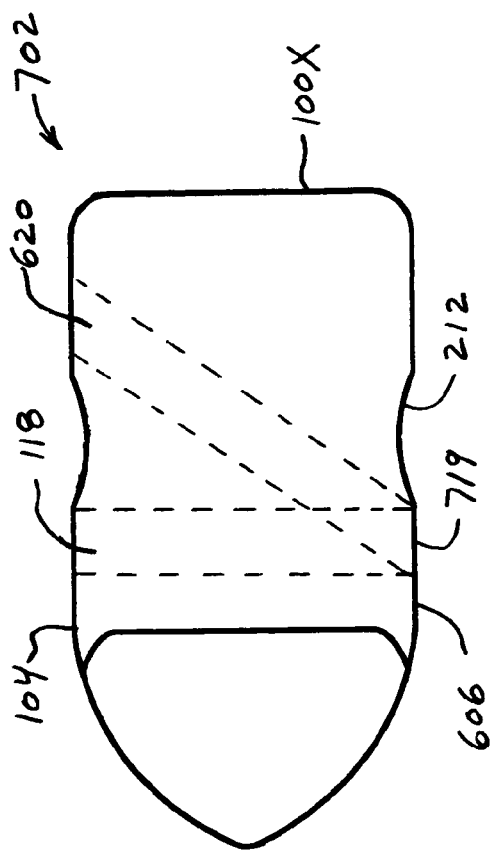
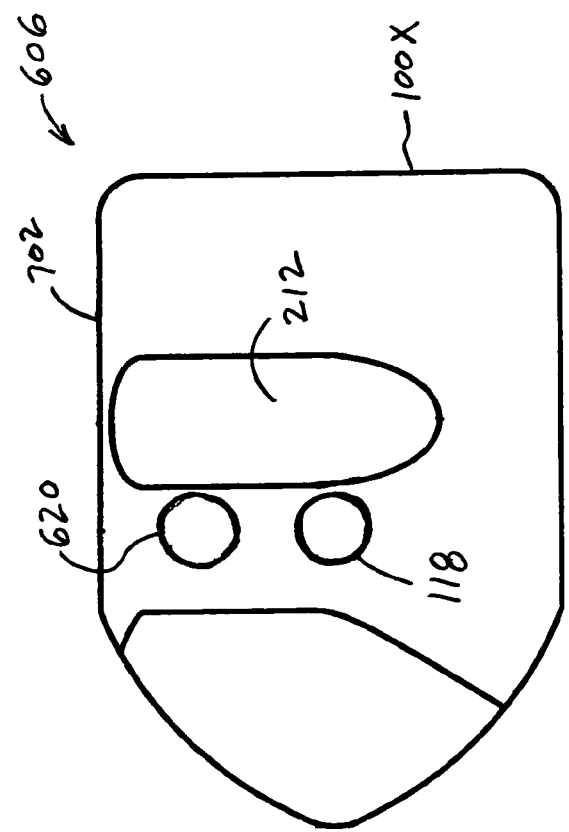
FIG. 7
FIG. 8

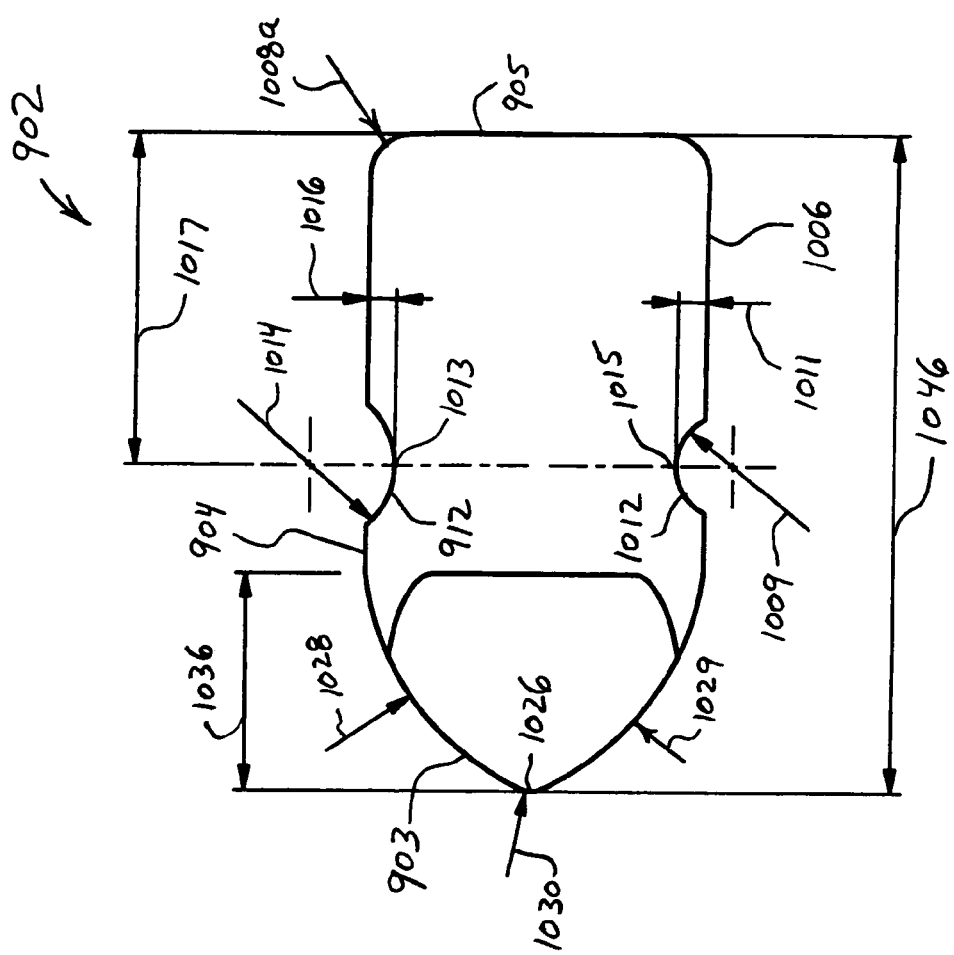
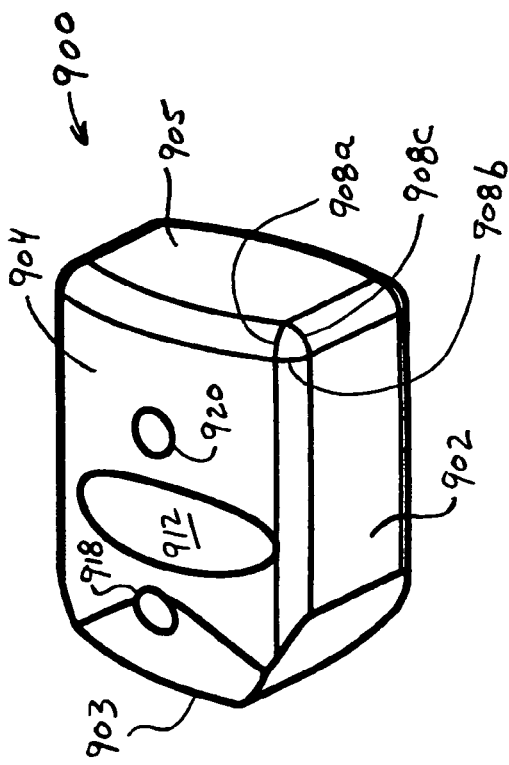
FIG. 10
FIG. 9

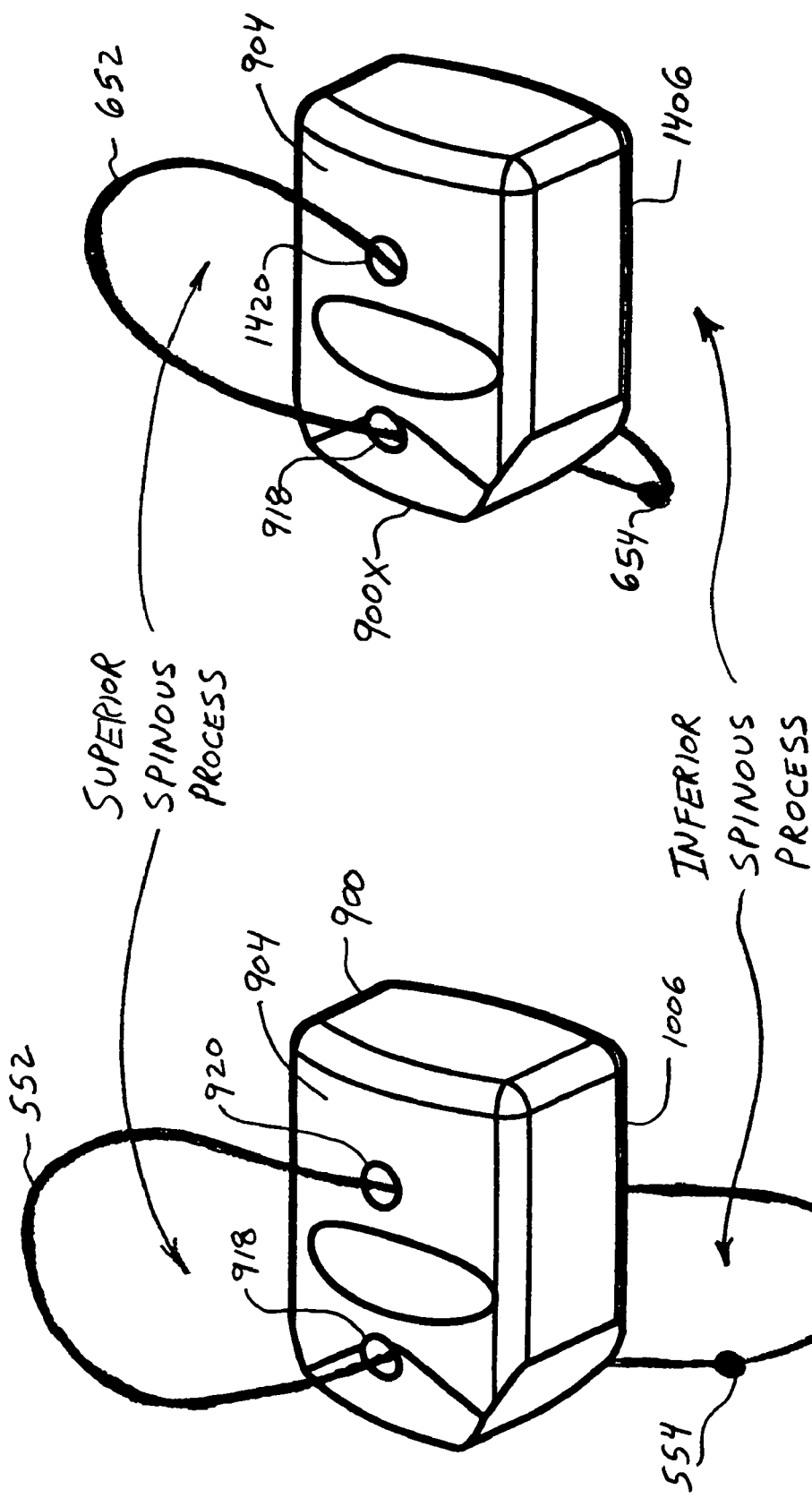

IMPLANT FOR SPINAL STABILIZATION AND ITS METHOD OF USE

CROSS REFERENCE TO RELATED APPLICATION

This claims the benefit of U.S. Provisional Application No. 60/688,359, filed Jun. 6, 2005.

TECHNICAL FIELD OF THE INVENTION

The invention relates to intra-spinous spacers that are inserted between two vertebrae to replace a damaged or degenerated spinal disc. More particularly, the invention relates to a spacer to be placed between the posterior spinous process of the spine and its method of use.

BACKGROUND OF THE INVENTION

Degenerative disc disease often results in a loss of disc height, which in turn can cause facet and nerve impingement. One standard of care is to remove the disc and fuse the two vertebrae together. However, this can lead to problems at adjacent vertebra levels as those levels become hypermobile to compensate for the loss of mobility at the fused level. A number of devices have therefore been developed to restore height without fusion. Such known devices include artificial discs, pedicle screws with flexible rods, and intra-spinous spacers. Known intra-spinous spacers are inserted between the posterior spinous process and can be made of solid or flexible material. Typically, known intra-spinous spacers are placed in the spine in slight distraction to off load the weight of the disc. Intra-spinous spacers also typically serve as a stop for extension, and some have attached straps that limit flexion. Many known intra-spinous spacers are in the shape of an H, wherein the sides of the H prevent the spacer from sliding out from between the processes. Known spacers also are usually made of a metal or a polymer. Ideally, however, bone would be a more suitable material for a spacer, but typical H-shaped bone spacers are likely to result undesirably in the vertebrae fusing to the spacer.

SUMMARY OF THE INVENTION

The device described herein is an intra-spinous spacer designed to be placed between the posterior spinous process. In one embodiment, the intra-spinous spacer is generally rectangularly-shaped and advantageously may be made of bone material, such as allograft or autograft. The spacer has top and bottom depressions for receiving the spinous process. The depressions advantageously reduce bone contact, which reduces, if not eliminates, the likelihood of bone fusion between adjacent vertebrae. The spacer may be formed solely of cortical bone and may be terminally sterilized to kill proteins.

The spacer may also include one or more fixation straps to secure the spacer laterally in place between the vertebrae. In one embodiment, the intra-spinous spacer may have one or more holes through the top and bottom surfaces to receive fixation straps. The fixation straps may be polyethylene or other biocompatible polymer and may be braided or unbraided. Other materials may include tendons or ligaments, or gracilis or semitendinousis. The strap(s) may be pretensioned prior to implantation, and where more than one strap is used, the straps may be preferably no more than 10 mm apart preferably to prevent slippage or rotation of the device. The straps may wrap around or surround the spacer. The strap(s) may be placed around one of the processes by forming a loop and may be locked or fixed to the spacer. The strap(s) may also be tacked, cemented, or otherwise secured to one of the processes. The strap(s) may be preferably about 70 mm long to wrap around one process and preferably about 140 mm long to wrap around both superior and inferior processes.

The spacer can be used to advantageously limit and preferably prevent both extension and flexion and may be secured to both the superior and inferior spinous processes, or limit and preferably prevent extension alone by being secured to only the superior spinous process, or limit and preferably prevent flexion alone by being secured to only the inferior spinous process.

In one embodiment, the spacer may have one or more openings or holes on the surface of the spacer to receive the straps and may further include a cover plate secured to the spacer for the straps. In one illustrative embodiment, the cover plate may be formed of bone and secured with pins made from bone. The cover plate may also be screwed into position. Alternatively, pins or screws may be used without a cover plate to secure the strap(s).

In one embodiment, the spacer is placed through the spinous ligament and in position between the spinous process at adjacent vertebrae. The supra-spinous ligament is not removed in this illustrative method of implanting the spacer. After the spacer is in position, one of the fixation straps is threaded or placed around the spinous process. If necessary, the other fixation strap, if provided, is threaded or placed around the other spinous process. Preferably, the fixation strap is placed first about the superior spinous process. Appropriate tension is placed on the straps, and the straps are locked into position. In one embodiment, a set screw or fixation pin is provided to lock the fixation strap into position. The spacer is preferably placed without adding any agents to promote bone growth, and the spacer may be coated with a material to resist or impede bone fusion of the spacer.

BRIEF DESCRIPTION OF THE DRAWINGS

The detailed description will be better understood in conjunction with the accompanying drawings, in which like reference characters represent like elements, as follows:

FIGS. 1-4 are perspective, front, side, and bottom views, respectively, of a first illustrative embodiment of a spinal process spacer according to the invention;

FIG. 5 is a perspective view of the spinal process spacer of FIGS. 1-4 illustrating a double-sided strapping;

FIG. 6 is a perspective view of an alternative embodiment of the spinal process spacer of FIGS. 1-5 illustrating a single-sided strapping;

FIGS. 7 and 8 are front and bottom views of the spinal process spacer of FIG. 6;

FIGS. 9-12 are perspective, front, side, and bottom views, respectively, of a second illustrative embodiment of a spinal process spacer;

FIG. 13 is a perspective view of the spinal process spacer of FIGS. 9-12 illustrating a double-sided strapping;

FIG. 14 is a perspective view of an alternative embodiment of the spinal process spacer of FIGS. 9-13 illustrating a single-sided strapping.

DETAILED DESCRIPTION OF THE INVENTION

Figure 4:
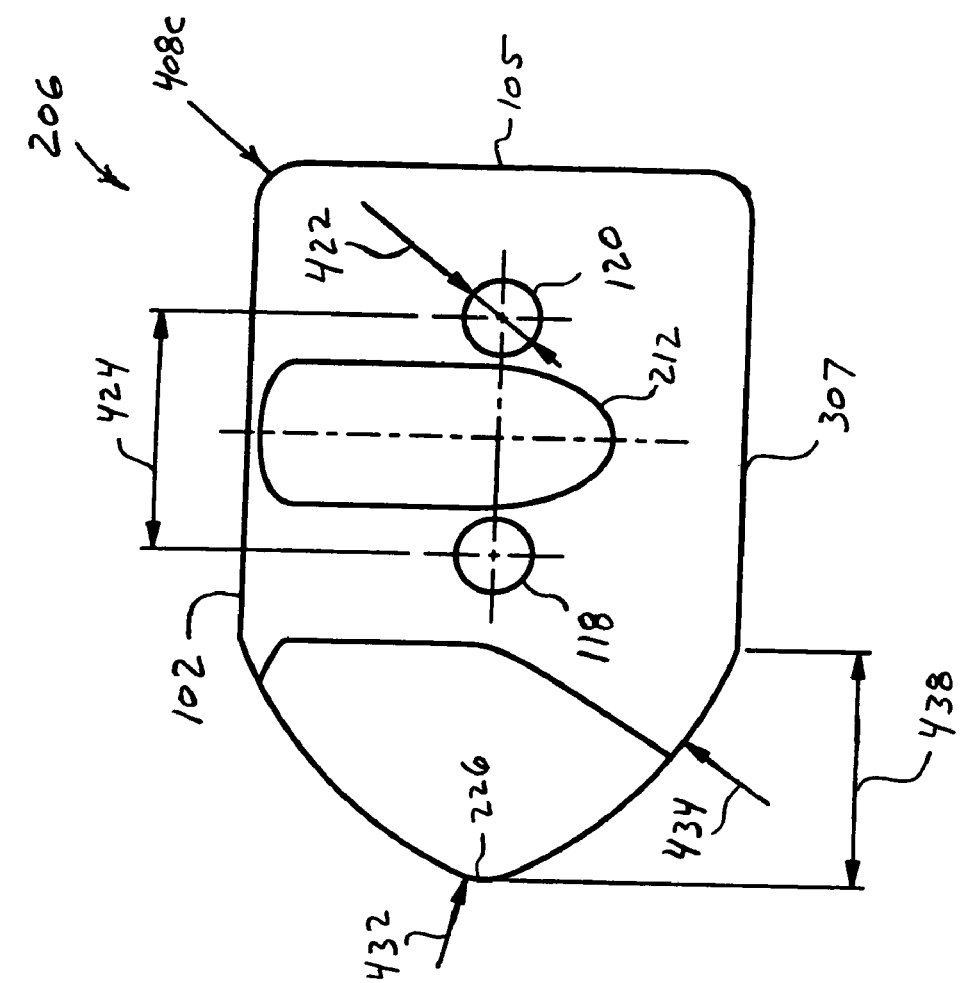

While an intra-spinous spacer is illustrated and described herein with reference to certain preferred or exemplary embodiments, the invention should not be limited to these preferred or exemplary embodiments. Furthermore, the features described and illustrated herein can be used singularly or in combination with other features and embodiments.

FIGS. 1-4 show a first embodiment of an intra-spinous spacer. Intra-spinous spacer 100 is preferably generally rectangular and has a front side 102, a nose side 103, a top side 104, an end side 105, a bottom side 206 (which in this embodiment is identical to top side 104), and a back side 307. (Note that the FIG. 3 view of nose side 103 is rotated 90° with respect to the FIG. 1 view to conform to the FIG. 4 view of bottom side 206—thus in FIG. 3, front side 102 is shown on top, top side 104 is shown on the left, and back side 307 is shown on the bottom.) Spacer 100 preferably has rounded edges 108a-c between the top side and the front, end, and back sides and between the bottom side and the front, end, and back sides. Radiuses 208a, 308b, and 408c of rounded edges 108a-c are each preferably about 1.5 mm. Alternatively, radiuses 208a, 308b, and 408c can be of other dimensions and do not have to be the same as each other.

Top side 104 has a depression 112 extending laterally across top side 104. Depression 112 is dimensioned and shaped to receive a spinous process, and preferably the spinous process contacts only depression 112 on top side 104. In one embodiment of the invention, bottom side 206 has an identical depression 212, which is also dimensioned and shaped to receive a spinous process, and also preferably the spinous process contacts only depression 212 on bottom side 206. Advantageously, depressions 112, 212 result in reduced and preferably minimized bone contact between spacer 100 and the vertebrae. Such reduced and minimized bone contact advantageously lowers, if not eliminates, the potential for bone fusion. Depression 112 preferably has a radius 214 of about 6 mm and a depth 216 into top side 104 of about 0.5 mm. In this embodiment, depression 212 has the same radius and depth. Alternatively, depressions 112, 212 can have other radiuses and depths and can have radiuses and depths different from each other. Also in this embodiment, the centers 213, 215 of depressions 112, 212 are positioned a distance 217 of about 9 mm from end side 105. Depressions 112, 212 alternatively may be positioned at other distances from end side 105.

Top side 104 also has a pair of holes 118, 120 for use with a fixation strap (described further below). Holes 118, 120 preferably extend completely through spacer 100 to bottom side 206. Alternatively, one or both of holes 118, 120 may be threaded to accept screwed fixation devices and may not extend completely through spacer 100. In an embodiment where one or both holes 118, 120 do not extend completely through spacer 100 from top side 104, bottom side 206 may have, for example, one or more threaded holes. In one embodiment of the invention, holes 118, 120 each have a diameter 422 of about 2.5 mm and are spaced apart by a center-to-center distance 424 of about 8 mm. Alternatively, holes 118, 120 can have other center-to-center distances and other diameters, which can be different from each other. Preferably, the center-to-center distances are not more than 10 mm apart. Moreover, spacer 100 alternatively can have other numbers of holes, and the holes need not be on top side 104 and/or bottom side 206.

Nose side 103 has a generally tapered shape and extends from the top, bottom, front, and back sides of spacer 100. Nose side 103 tapers distally and inwardly (preferably toward the center of nose side 103) from the top, bottom, front, and back sides to form a generally pointed or rounded distal tip 226. Nose side 103 preferably has four surfaces that smoothly and continuously join together from the top, bottom, front, and back sides, respectively, with preferably no sharp boundary edges. Representative radiuses of nose side 103 are as follows: radius 228, which curves down from top side 104, is about 10 mm. Preferably, radius 229, which curves up from bottom side 206, is also about 10 mm. Radius 230 is about 1 mm, while radius 432 is about 2 mm. Radius 434, which curves inward from back side 307 is about 14 mm. The distally and inwardly tapering portion of nose side 103 has a length 236, measured from front side 102, of about 8 mm and a length 438, measured from the top and bottom sides, of also about 8 mm. Alternatively, nose side 103 can be of other dimensions.

Figure 3:
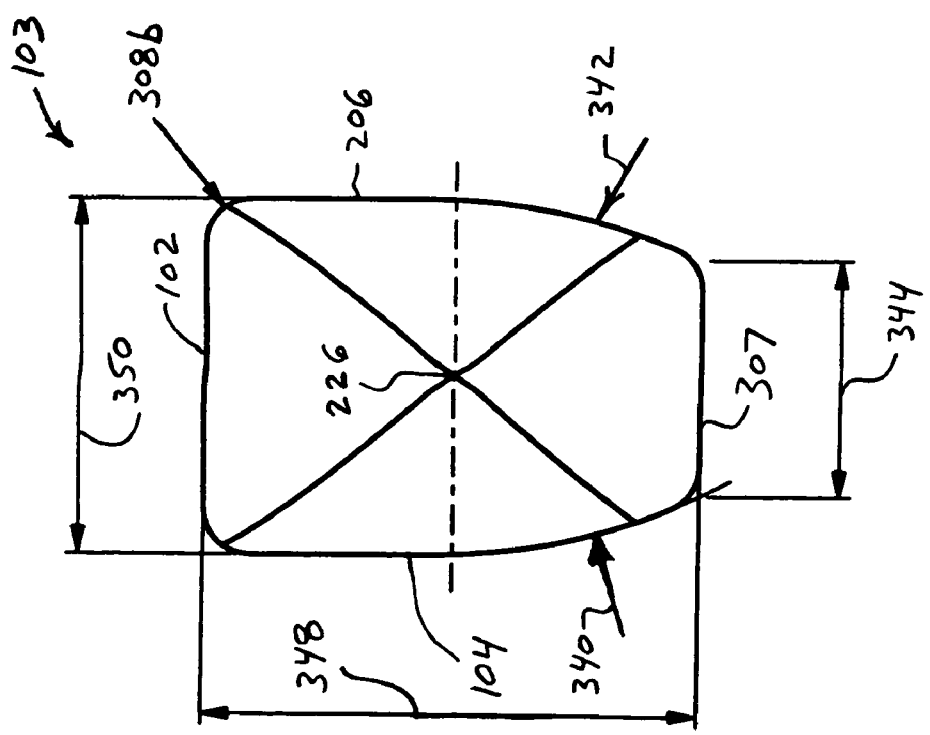
Figure 12:
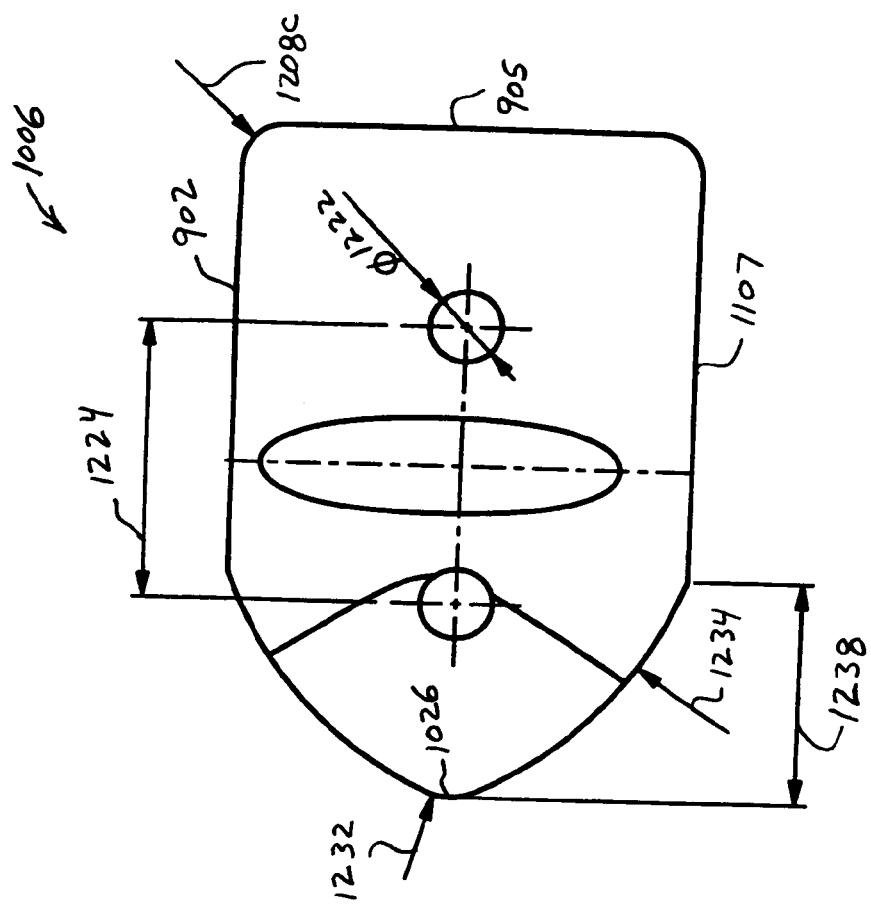

Referring in particular to FIG. 3, top side 104 and bottom side 206 each has a portion (starting at preferably halfway on each side) that curves inwardly toward back side 307 at respective radiuses 340, 342 of about 20 mm each. Back side 307 has a width 344 of about 8 mm. In other embodiments of the invention, radiuses 340, 342 and width 344 can be of other values.

Spacer 100 has a length 246, a width 348, and a thickness 350. In the embodiment shown in FIGS. 1-4, length 246 is preferably about 24 mm. Width 348 and thickness 350 are preferably dimensionally paired and variable depending on the spinal application. Preferably, the spacers are provided in a variety of sizes with thickness 350 increasing in 2 mm increments. Illustrative representative thicknesses can be about 6 mm to about 16 mm. Preferably, width 348 is about 4 mm greater than the thickness. Illustrative representative widths can be about 10 mm to about 20 mm. For example, width 348 may be about 10 mm, while thickness 350 may be about 6 mm. Or, width 348 may be about 20 mm, while thickness 350 may be about 16 mm. Other possible dimensions include a width 348 of about 16 mm and a thickness 350 of about 12 mm. Alternatively, spacer 100 may be of other lengths, widths, and thicknesses.

Spacer 100 may be made of biocompatible materials such as, for example, PEAK, polycarbonate urethane, silicon polycarbonate urethane, or other polymer and plastic materials. The spacer may also be made of metals, such as, for example, titanium or stainless steel, and may also be made of composites, ceramics, or combinations of materials. Preferably, spacer 100 is made from bone and more preferably solely from cortical bone. Cortical bone reduces and preferably minimizes the possibility of bone fusion. Spacer 100 may be provided with a coating to minimize, resist, or prevent the possibility of bone fusion.

FIG. 5 illustrates spacer 100 having a fixation strap extending from top side 104 for the superior spinous process and a fixation strap extending from bottom side 206 for the inferior spinous process. A fixation strap 552 may be first looped around a superior spinous process over top side 104, inserted through hole 118 or 120, looped around an inferior spinous process under bottom side 206, inserted through the other of hole 118 or 120, and then tightened and tied together as shown at location 554. Note that fixation strap 552 can be tied together at other suitable or preferred locations. In an alternative method, strap 552 may be first looped around the superior spinous process, one end of the strap may then be inserted through one of holes 118 or 120, the other end of the strap inserted through the other of holes 118 or 120, one end of the strap looped around the inferior spinal process, and the strap then tightened and secured together. In yet another alternative method, fixation strap 552 may be looped around one of the superior or inferior spinous processes, one end of the strap inserted through hole 118, the other end inserted through hole 120, and the ends secured to either the spacer or the other spinous process. While the spacer has been shown with a single fixation strap to secure both the superior and inferior spinous processes, note that separate and multiple fixation straps can be used instead. A double-sided strapping of spacer 100, as shown in FIG. 5, limits and preferably prevents both flexion and extension.

FIG. 6 illustrates a single-sided strapping of an alternative embodiment of spacer 100 to a superior spinous process. A fixation strap 652 is looped around a superior spinous process over top side 104 of spacer 100*x*, inserted through holes 118 and 620, and then tightened and tied together under bottom side 606 at location 654. Alternatively, strap 652 can be tied at other suitable or more preferred locations. A single-sided strapping of spacer 100*x* bypasses the inferior spinous process and accordingly limits, and preferably prevents, extension alone. Note that the same single-sided strapping spacer may be used for attachment to the inferior spinous process instead of the superior spinous process.

Spacer 100*x* is substantially identical to spacer 100. In spacer 100, holes 118 and 120 extend substantially straight through from top side 104 to bottom side 206. In spacer 100*x*, as shown in FIGS. 7 and 8, hole 118 also extends substantially straight through from top side 104 to bottom side 606. However, hole 620 extends diagonally through spacer 100*x* from top side 104 to bottom side 606 (as best seen in FIG. 7 via front side 702). Note that diagonal hole 620 alternatively may have a common opening 719 with straight hole 118 on bottom side 606. Diagonal hole 620 advantageously allows fixation strap 652 to be used with a superior spinous process without interfering with the inferior spinous process, which is received in depression 212, or vice versa.

Fixation straps 552 and 652 may be made of polyethylene or other biocompatible polymer. They may also be wires, monofilaments, or tendons or ligaments, such as the gracilis or semitendinousis (located around the knee). Tendon fixation straps may be pretensioned prior to implant, and fixation straps may also be braided. Furthermore, the straps may be elastic or inelastic, but preferably are flexible to assist with the placement around the spinous process. In general, fixation straps should be about 120-140 mm in length, but can be of other lengths in accordance with the application. For example, the fixation strap of FIG. 5 may be about 140 mm, and the fixation strap of FIG. 6 may be about 70 mm. Preferably spacers 100/100*x* are supplied with fixation straps 552/652, respectively, pre-threaded through hole 118, hole 120/620, or both prior to implantation.

FIGS. 9-12 show a second embodiment of an intra-spinous spacer. Intra-spinous spacer 900 also is preferably generally rectangular and has a front side 902, a nose side 903, a top side 904, an end side 905, a bottom side 1006 (which in this embodiment is not identical to top side 904), and a back side 1107. (Note that the FIG. 11 view of nose side 903 is rotated 90° with respect to the FIG. 9 view to conform to the FIG. 12 view of bottom side 1006—thus in FIG. 11, front side 902 is shown on top, top side 904 is shown on the left, and back side 1107 is shown on the bottom.) Spacer 900 preferably has rounded edges 908*a-c* between the top side and the front, end, and back sides and between the bottom side and the front, end, and back sides. Radiuses 1008*a*, 1108*b*, and 1208*c* of rounded edges 908*a-c* are each preferably about 1.5 mm. Alternatively, radiuses 1008*a*, 1108*b*, and 1208*c* can be of other dimensions and do not have to be the same as each other.

Top side 904 has a depression 912 extending laterally across top side 904. Depression 912 is dimensioned and shaped to receive a spinous process, and preferably the spinous process contacts only depression 912 on top side 904. Bottom side 1006 has a depression 1012, which is also dimensioned and shaped to receive a spinous process, and also preferably the spinous process contacts only depression 1012 on bottom side 1006. Advantageously, depressions 912, 1012 result in reduced and preferably minimized bone contact between spacer 900 and the vertebrae. Such reduced and minimized bone contact advantageously lowers, if not eliminates, the potential for bone fusion. Spacer 900 may be provided with a coating to minimize, resist, or prevent the possibility of bone fusion. Depression 912 preferably has a radius 1014 of about 3 mm and a depth 1016 into top side 904 of about 1 mm. Depression 1012 has a radius 1009 of about 2 mm and the same depth 1011 into bottom side 1006 of about 1 mm. Alternatively, depressions 912, 1012 can have other radiuses and depths, including radiuses and depths that are the same as or different from each other. Also in this embodiment, the centers 1013, 1015 of depressions 912, 1012 are positioned a distance 1017 of about 12 mm from end side 905. Depressions 912, 1012 alternatively may be positioned at other distances from end side 905.

Top side 904 also has a pair of holes 918, 920 for use with a fixation strap (described further below). Holes 918, 920 preferably extend completely through spacer 900 to bottom side 1006. Alternatively, one or both of holes 918, 920 may be threaded to accept screwed fixation devices and may not extend completely through spacer 900. In an embodiment where one or both holes 918, 920 do not extend completely through spacer 900 from top side 904, bottom side 1006 may have, for example, one or more threaded holes. In one embodiment of the invention, holes 918, 920 each have a diameter 1222 of about 2.5 mm and are spaced apart by a center-to-center distance 1224 of about 10 mm. Alternatively, holes 918, 920 can have other center-to-center distances and other diameters, which can be different from each other. Moreover, spacer 900 alternatively can have other numbers of holes, and the holes need not be on top side 904 and/or bottom side 1006.

Nose side 903 has a generally tapered shape and extends from the top, bottom, front, and back sides of spacer 900. Nose side 903 tapers distally and inwardly (preferably toward the center of nose side 103) from the top, bottom, front, and back sides to form a generally pointed or rounded distal tip 1026. Nose side 903 preferably has four surfaces that smoothly and continuously join together from the top, bottom, front, and back sides, respectively, with preferably no sharp boundary edges. Representative radiuses of nose side 903 are as follows: radius 1028, which curves down from top side 904, is about 10 mm. Preferably, radius 1029, which curves up from bottom side 1006, is also about 10 mm. Radius 1030 is about 1 mm, while radius 1232 is about 2 mm. Radius 1234, which curves inward from back side 1107 is about 14 mm. The distally and inwardly tapering portion of nose side 903 has a length 1036, measured from front side 902, of about 8 mm and a length 1238, measured from the top and bottom sides, of also about 8 mm. Alternatively, nose side 903 can be of other dimensions.

Figure 11:
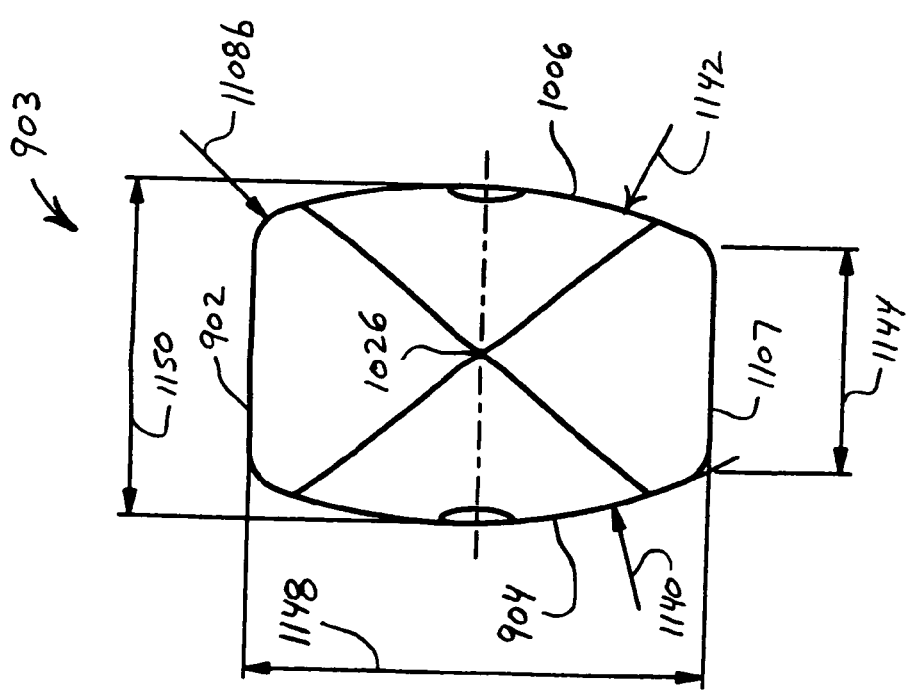

Referring in particular to FIG. 11, top side 904 and bottom side 1006 each has a portion (starting preferably halfway on each side) that curves inwardly toward back side 1107 at respective radiuses 1140, 1142 of about 20 mm each. Back side 1107 has a width 1144 of about 8 mm. In other embodiments of the invention, radiuses 1140, 1142 and width 1144 can be of other values.

Spacer 900 has a length 1046, a width 1148, and a thickness 1150. In the embodiment shown in FIGS. 9-12, length 1046 is preferably about 24 mm. Width 1148 and thickness 1150 are preferably dimensionally paired and variable depending on the spinal application. Preferably, the spacers are provided in a variety of sizes with thickness 1150 increasing in 2 mm increments. Illustrative representative thicknesses can be about 6 mm to about 16 mm. Preferably, width 1148 is about 4 mm greater than the thickness. Illustrative representative widths can be about 10 mm to about 20 mm. For example, width 1148 may be about 10 mm, while thickness 1150 may be about 6 mm. Or, width 1148 may be about 20 mm, while thickness 1150 may be about 16 mm. Other possible dimensions include a width 348 of about 14 mm and a thickness 1150 of about 10 mm. Alternatively, spacer 900 may be of other lengths, widths, and thicknesses.

As spacer 100, spacer 900 also may be made of biocompatible materials such as, for example, PEAK, polycarbonate urethane, silicon polycarbonate urethane, or other polymer and plastic materials. The spacer may also be made of metals, such as, for example, titanium or stainless steel, and may also be made of composites, ceramics, or combinations of materials. Preferably, spacer 900 is made from bone and more preferably solely from cortical bone. Spacer 900 may be provided with a coating to minimize, resist, or prevent the possibility of bone fusion.

When inserted, the shapes of spacers 100 and 900 preferably cause the spacers to be pushed back towards the spinal column for a better fit between the vertebrae.

FIG. 13 illustrates a double-sided strapping of spacer 900 to a superior spinous process and an inferior spinous process. Fixation strap 552 may be first looped around a superior spinous process over top side 904, inserted through one of holes 918 or 920, looped around an inferior spinous process under bottom side 1006, inserted through the other of holes 918 or 920, and then tightened and secured together as shown at location 554. Note that fixation strap 552 can be secured together at other suitable or preferred locations. In an alternative method, strap 552 may be first looped around the superior spinous process, one end of the strap may then be inserted through one of holes 918 or 920, the other end of the strap inserted through the other of holes 918 or 920, one end of the strap looped around the inferior spinal process, and the strap then tightened and secured together. In yet another alternative method, fixation strap 552 may be looped around one of the superior or inferior spinous processes, one end of the strap inserted through hole 918, the other end inserted through hole 920, and the ends secured to either the spacer or the other spinous process. While the spacer has been shown with a single fixation strap to secure both the superior and inferior spinous processes, note that separate and multiple fixation straps can be used instead. A double-sided strapping of spacer 900 limits, and preferably prevents, both flexion and extension.

FIG. 14 illustrates a single-sided strapping of an alternative embodiment of spacer 900 to a superior spinous process. Fixation strap 652 is looped around a superior spinous process over top side 904 of spacer 900x, inserted through holes 918 and 1420, and then tightened and tied together. Strap 652 may be tied and joined under bottom side 1406 at location 654. Alternatively, strap 652 can be tied at other suitable or more preferred locations. A single-sided strapping of spacer 900x bypasses the inferior spinous process and accordingly limits, and preferably prevents, extension alone. Note that the same single-sided strapping spacer may be used for attachment to the inferior spinous process instead of the superior spinous process.

Preferably spacers 900/900x are supplied with fixation straps 552/652, respectively, pre-threaded through hole 918, hole 920/1420, or both prior to implantation.

Figure 15:
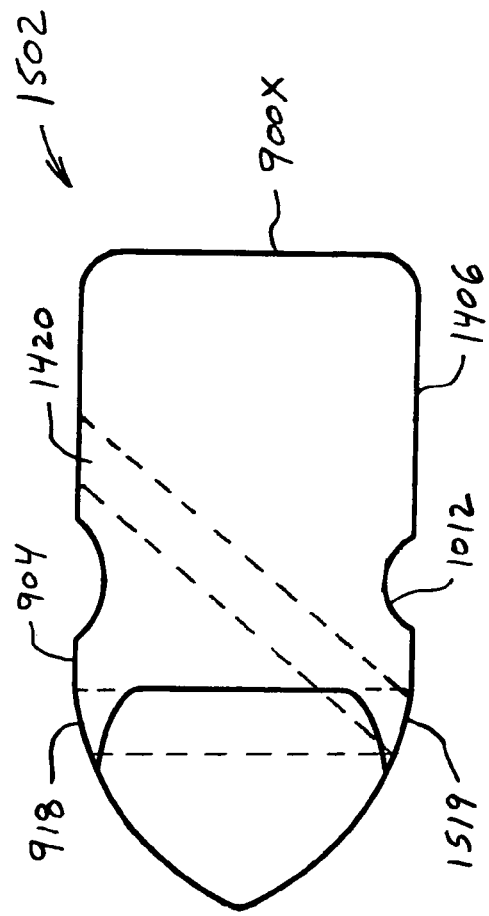
FIGS. 15 and 16 are front and bottom views of the spinal process spacer of FIG. 14.
Figure 16:
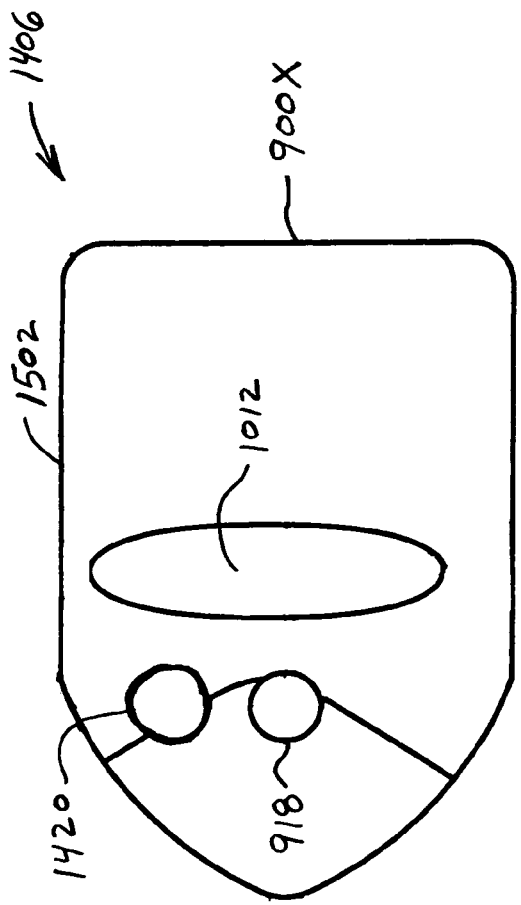

Spacer 900x is substantially identical to spacer 900. In spacer 900, holes 918 and 920 extend substantially straight through from top side 904 to bottom side 1006. In spacer 900x, as shown in FIGS. 15 and 16, hole 918 also extends substantially straight through from top side 904 to bottom side 1406. However, hole 1420 extends diagonally through spacer 900x from top side 904 to bottom side 1406 (as best seen in FIG. 15 via front side 1502). Note that diagonal hole 1420 alternatively may have a common opening 1519 with straight hole 918 on bottom side 1406. Diagonal hole 1420 advantageously allows fixation strap 652 to be used with a superior spinous process without interfering with the inferior spinous process, which is received in depression 1012, or vice versa.

Spacers 100, 100x, 900, and 900x are preferably terminally sterilized, preferably by chemical or other appropriate processes, prior to implantation to kill proteins.

Furthermore, the depressions of spacers 100, 100x, 900, and 900x may be lined with an inert material, such as, for example, silicone.

Also note that spacers of the invention may include a cover plate made preferably of bone material and secured to the spacer preferably with bone pins. Cover plates may include recesses for wrapping a fixation strap around the spacer. Additionally or alternatively, fixation straps may be fixed to a cover plate with one or more set screws.

Further note that while holes are shown in the spacers, other means may be alternatively used to secure one or more fixation straps. For example, fixation straps may be secured or tacked to the spacer or spinous process using, for example, bone pins, screws, or other suitable means.

While it is apparent that the illustrative embodiments of the invention disclosed herein fulfill the objectives stated above, it will be appreciated that numerous modifications and other embodiments may be devised by those skilled in the art. Features and structures, such as, for example, the size, shape, and location of the spacer depressions can be used singularly or in combination with other features and structures. Therefore, it will be understood that the appended claims are intended to cover all such modifications and embodiments which come within the spirit and scope of the invention.

I claim:

1. An intra-spinous spacer for implantation between spinous processes of the spine, the spacer comprising:
 a body having a top side, a bottom side opposite the top side, a front side, a back side opposite the front side, an end side, and a nose side opposite the end side, the front, back, end, and nose sides between the top and bottom sides; wherein:
 the nose side is formed by first, second, third and fourth radius surfaces that taper to a pointed or rounded tip, the first surface joined to the top side, the second surface joined to the bottom side, the third surface joined to the front side and the fourth surface joined to the back side, the first surface joins to the second surface and the third surface joins to the fourth surface at the tip;
 the top side has a first depression configured such that a spinous process contacts only the first depression on the top side in an implanted position, the top side further includes first and second holes formed therein, the first and second holes extending through the body from the top side to the bottom side, the first depression being located between the first and second holes formed on the top side; and
 the bottom side has a second depression configured such that an adjacent spinous process contacts only the second depression on the bottom side in the implanted position, one of the first and second holes extending diagonally though the body such that the first and second holes exit the body at the bottom side through a single common opening, the second depression being located to one side of the single common opening; and at least one fixation strap for securing the spacer to at least one spinous process, the at least one fixation strap passing through the first and second holes.

2. The intra-spinous spacer of claim 1 wherein the body has a length, a width, and a thickness of about 4 mm less than the width.

3. The intra-spinous spacer of claim 1 wherein the body has a length of about 24 mm, a width ranging from 10 mm to 20 mm, and a thickness of about 4 mm less than the width.

4. The intra-spinous spacer of claim 1 wherein the body has a length of about 24 mm, a width of about 10 mm, and a thickness of about 6 mm.

5. The intra-spinous spacer of claim 1 wherein the first and second depressions are identically sized and shaped.

6. The intra-spinous spacer of claim 1 wherein the first depression has a radius of about 6 mm and a depth into the top side of about 0.5 mm.

7. The intra-spinous spacer of claim 1 wherein the first depression has a radius of about 3 mm and a depth into the top side of about 1.0 mm.

8. The intra-spinous spacer of claim 7 wherein the second depression has a radius of about 2 mm and a depth into the bottom side of about 1.0 mm.

9. The intra-spinous spacer of claim 1 wherein the top side is bounded by two lateral edges and two longitudinal edges and the first depression has a center located about 9 mm or 12 mm from one of the lateral edges.

10. The intra-spinous spacer of claim 1 wherein the fixation strap is a tendon.

11. The intra-spinous spacer of claim 1 wherein the fixation strap has a length of about 70 mm or about 120 mm to 140 mm.

12. The intra-spinous spacer of claim 1 wherein the tip has a radius of curvature between and perpendicular to the top and bottom sides of about 1 mm.

13. The intra-spinous spacer of claim 1 wherein each of the radius surfaces has a length about 8 mm.

14. The intra-spinous spacer of claim 1 wherein the radius surface associated with the top side has a radius of curvature of about 10 mm, the radius surface associated with the bottom side has a radius of curvature of about 10 mm, and the radius surfaces associated with the front and back sides have a radius of curvature of about 14 mm.

15. The intra-spinous spacer of claim 1 wherein the spacer comprises cortical bone.

* * * * *